US011551791B2

(12) United States Patent
Tapadar et al.

(10) Patent No.: US 11,551,791 B2
(45) Date of Patent: Jan. 10, 2023

(54) KEY NOTE

(71) Applicant: CERNER INNOVATION, INC., Kansas City, KS (US)

(72) Inventors: Soumen Tapadar, Karnataka (IN); Gaurav Saini, Haryana (IN)

(73) Assignee: CERNER INNOVATION, INC., North Kansas City, MO (US)

( * ) Notice: Subject to any disclaimer, the term of this patent is extended or adjusted under 35 U.S.C. 154(b) by 0 days.

(21) Appl. No.: 16/852,730

(22) Filed: Apr. 20, 2020

(65) Prior Publication Data

US 2021/0327546 A1    Oct. 21, 2021

(51) Int. Cl.
*G16H 10/60* (2018.01)
*G06F 3/0482* (2013.01)
*H04L 67/02* (2022.01)
*G06F 9/451* (2018.01)

(52) U.S. Cl.
CPC ............ *G16H 10/60* (2018.01); *G06F 3/0482* (2013.01); *G06F 9/451* (2018.02); *H04L 67/02* (2013.01)

(58) Field of Classification Search
CPC ....... G06F 3/0482; G06F 9/451; G16H 10/60; H04L 67/02
See application file for complete search history.

(56) References Cited

U.S. PATENT DOCUMENTS

| | | | | |
|---|---|---|---|---|
| 5,404,435 | A * | 4/1995 | Rosenbaum | G06F 16/40 715/205 |
| 8,276,090 | B2 * | 9/2012 | Chen | G06F 9/543 715/770 |
| 9,864,502 | B1 * | 1/2018 | Kuruba | G06F 3/0483 |
| 2006/0080142 | A1 * | 4/2006 | Hart | G16H 10/60 705/2 |
| 2008/0133600 | A1 * | 6/2008 | Uehori | G06Q 10/10 |
| 2009/0237855 | A1 * | 9/2009 | Shrier | H05K 1/167 361/126 |
| 2012/0084092 | A1 * | 4/2012 | Kozuch | G16H 10/60 705/2 |
| 2012/0109686 | A1 * | 5/2012 | Higbie | G16H 10/60 705/3 |
| 2012/0131507 | A1 * | 5/2012 | Sparandara | G16H 10/60 715/833 |
| 2012/0233151 | A1 * | 9/2012 | Vanderwende | G06F 16/954 707/722 |

(Continued)

*Primary Examiner* — Eric J. Bycer
(74) *Attorney, Agent, or Firm* — Shook, Hardy and Bacon L.L.P.

(57) ABSTRACT

Methods, computer systems, and computer storage media are provided that enables clinicians to create and interact with snapshots of critical clinical/non-clinical information that is readily accessible in future visits. Initially, an indication to create a key note corresponding to a clinical note of a patient encounter for a patient is received. A selection of a key note section that will be associated with the key note is also received. Upon the clinical note being signed, the key note is created and saved. Upon receiving a request from a user, a key note window is provided in a user interface. The user interface enables the user to expand a header corresponding to a particular key note to display details associated with the corresponding encounter. A hyperlink to original summary notes from which the particular key note was created may be provided by the user interface.

20 Claims, 16 Drawing Sheets

(56) References Cited

U.S. PATENT DOCUMENTS

| | | | | |
|---|---|---|---|---|
| 2012/0233534 A1* | 9/2012 | Vanderwende | ....... | G06F 40/279 715/230 |
| 2013/0124978 A1* | 5/2013 | Horns | .................. | G06F 40/169 715/243 |
| 2015/0370768 A1* | 12/2015 | Tigchelaar | ............ | G06F 40/166 715/254 |
| 2016/0026720 A1* | 1/2016 | Lehrer | .................... | G06F 16/23 707/710 |
| 2016/0321404 A1* | 11/2016 | Ginsburg | ............ | G06F 3/04842 |
| 2017/0116373 A1* | 4/2017 | Ginsburg | ............... | G16H 40/20 |
| 2017/0124039 A1* | 5/2017 | Hailpern | ............... | G06F 40/134 |
| 2017/0132371 A1* | 5/2017 | Amarasingham | ....... | G06F 40/30 |
| 2017/0235888 A1* | 8/2017 | Rahman | ................ | G06F 40/295 705/3 |
| 2018/0101651 A1* | 4/2018 | Buckley | ................. | G16H 50/70 |
| 2021/0035664 A1* | 2/2021 | Lirov | ..................... | G06F 9/451 |

* cited by examiner

KEY NOTE

BACKGROUND

When a patient visits a hospital, prior to the patient/clinician encounter, the clinician typically reviews a summary of all previous visits to gain an understanding of the background for the present visit. In many cases, this requires the patient to obtain and provide numerous documents or information at the beginning of the visit. Even with widespread electronic medical record (EMR) availability, clinicians still have to sort through large amounts of data spread throughout documentation from previous visits to understand the patient visit background. As this consists of both demographic and clinical data, this can be a time-consuming task.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to enabling clinicians to create and interact with snapshots of encounters with patients. More particularly, the present invention enables clinicians to create and interact with snapshots (i.e., key notes) of critical clinical/non-clinical information that is readily accessible in future visits. Initially, an indication to create a key note corresponding to a clinical note of a patient encounter for a patient is received. A selection of a key note section that will be associated with the key note is also received. Upon the clinical note being signed, the key note is created and saved. The key note is visible upon a key note window being launched. After the key note section is selected, the key note details corresponding to the patient encounter are provided.

In some embodiments, upon receiving a request from a user, the key note window is provided in a user interface. The key note window displays a header corresponding to the key note and any additional key notes that have been created and saved for the patient. The header may comprise an encounter date, a diagnosis, and a type of encounter. The key note and any additional key notes may be presented in the key note window in chronological order corresponding to an encounter date of each key note. The user interface enables a user to expand the header corresponding to a particular key note to display details associated with the corresponding encounter. A hyperlink to original summary notes from which the particular key note was created may be provided by the user interface. Upon receiving a selection of the hyperlink, the original summary notes may be provided to the user.

BRIEF DESCRIPTION OF THE SEVERAL VIEWS OF THE DRAWINGS

The present invention is described in detail below with reference to the attached drawing figures, wherein:

FIGS. 3-14 depict illustrative screen displays, in accordance with embodiments of the present invention;

DETAILED DESCRIPTION

Figure 1:
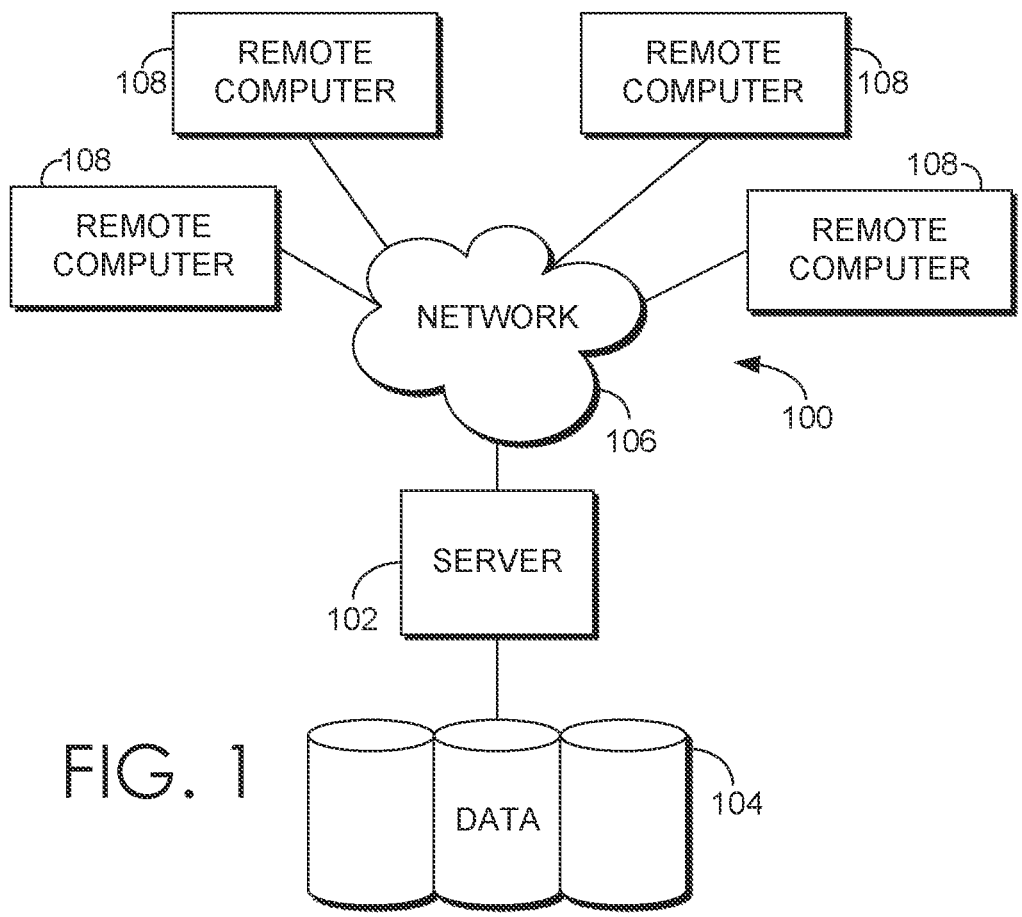
FIG. 1 is a block diagram of an exemplary computing environment suitable for use in implementing the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

As noted in the Background, when a patient visits a hospital, prior to the patient/clinician encounter, the clinician typically reviews a summary of all previous visits to gain an understanding of the background for the present visit. In many cases, this requires the patient to obtain and provide numerous documents or information at the beginning of the visit. Even with widespread EMR availability, clinicians still have to sort through large amounts of data spread throughout documentation from previous visits to understand the patient visit background. As this consists of both demographic and clinical data, this can be a time-consuming task.

Embodiments of the present invention relate to enabling clinicians to create and interact with snapshots of encounters with patients. To do so, the present invention enables clinicians to create and interact with snapshots (i.e., key notes) of critical clinical/non-clinical information that is readily accessible in future visits. Initially, an indication to create a key note corresponding to a clinical note of a patient encounter for a patient is received. A selection of a key note section that will be associated with the key note is also received. Upon the clinical note being signed, the key note is created and saved. The key note is visible upon a key note window being launched. After the key note section is selected, the key note details corresponding to the patient encounter are provided.

In some embodiments, upon receiving a request from a user, the key note window is provided in a user interface. The key note window displays a header corresponding to the key note and any additional key notes that have been created and saved for the patient. The header may comprise an encounter date, a diagnosis, and a type of encounter. The key note and any additional key notes may be presented in the key note window in chronological order corresponding to an encounter date of each key note. The user interface enables a user to expand the header corresponding to a particular key note to display details associated with the corresponding encounter. A hyperlink to original summary notes from which the particular key note was created may be provided by the user interface. Upon receiving a selection of the hyperlink, the original summary notes may be provided to the user.

In embodiments, key notes enables clinicians to easily select the patient data/information/text from an enormous amount of available patient data. In embodiments, key notes provide clinicians the ability to select clinical data/information/text of the current patient visit, which might have importance in the treatment for upcoming visits. In embodiments, key notes provide clinicians the ability to bifurcate the data to be added based on the type of data enabling the data to be presented in a meaningful way under an appropriate section (e.g., diagnosis, medications, and the like). In embodiments, key notes provide clinicians an option to create a customized section to be added for a key note. In embodiments, key notes provide a quick snapshot of a patient's previous visits to a clinician. In embodiments, key notes enable clinicians to save time previously required to review data for previous visits, as only important data captured by clinicians is included in key notes which are made available in a single user interface. This also reduces the amount of CPU and memory required by the system providing the key notes compared to a system requiring a clinician to sort through an entire EMR or other health information systems for similar data. In embodiments, key notes improve clinician and patient satisfaction, as each clinician is able to reduce time spent reviewing historical data and increase time spent interacting with patients. Moreover, patient satisfaction can be increased as treatments may be provided in a more timely fashion.

Accordingly, in one aspect, an embodiment is directed to one or more computer storage media having computer-executable instructions embodied thereon that, when executed by a computer, causes the computer to perform operations. The operations receiving an indication to create a key note corresponding to a clinical note of a patient encounter for a patient. The operations also include receiving a selection of a key note section that will be associated with the key note. The operations further include, upon the clinical note being signed, creating and saving the key note, the key note being visible upon a key note window being launched and the key note section being selected to view key note details corresponding to the patient encounter.

In another aspect of the invention, an embodiment of the present invention is directed to a computerized method. The method includes receiving an indication to create a key note corresponding to a clinical note of a patient encounter for a patient. The method also includes receiving a selection of a key note section that will be associated with the key note. The method further includes, upon the clinical note being signed, creating and saving the key note, the key note being visible upon a key note window being launched and the key note section being selected to view key note details corresponding to the patient encounter.

In a further aspect, an embodiment is directed to a computerized system that includes one or more processors and a non-transitory computer storage medium storing computer-useable instructions that, when used by the one or more processors, cause the one or more processors to: receive an indication to create a key note corresponding to a clinical note of a patient encounter for a patient; receive a selection of a key note section that will be associated with the key note; upon the clinical note being signed, create and save the key note, the key note being visible upon a key note window being launched and the key note section being selected to view key note details corresponding to the patient encounter; and upon receiving a request from a user, provide the key note window in a user interface, the key note window displaying a header corresponding to the key note and any additional key notes that have been created and saved for the patient.

Having briefly described embodiments of the present invention, an exemplary operating environment suitable for use in implementing embodiments of the present invention is described below. FIG. 1 provides an aspect of an example operating environment with which embodiments of the present invention may be implemented. The aspect of an operating environment is illustrated and designated generally as reference numeral 100.

Example operating environment 100 comprises a general purpose computing device in the form of a control server 102. Exemplary components of the control server 102 comprise a processing unit, internal system memory, and a suitable system bus for coupling various system components, including database cluster 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Control server 102 typically includes therein, or has access to, a variety of computer-readable media, for instance, database cluster 104. Computer-readable media can be any available media that might be accessed by control server 102, and includes volatile and nonvolatile media, as well as, removable and nonremovable media. Computer-readable media might include computer storage media. Computer storage media includes volatile and nonvolatile media, as well as removable and nonremovable media implemented in any method or technology for storage of information, such as computer-readable instructions, data structures, program modules, or other data. In this regard, computer storage media might comprise RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 102. Computer storage media does not comprise signals per se. Combinations of any of the above also may be included within the scope of computer-readable media.

The computer storage media discussed above and illustrated in FIG. 1, including database cluster 104, provide storage of computer-readable instructions, data structures, program modules, and other data for the control server 102. In some embodiments, data cluster 104 takes the form of a cloud-based data store, and in some embodiments is accessible by a cloud-based computing platform.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and providers' offices. Providers may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like.

The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Exemplary computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networked environment, program modules or portions thereof might be stored in association with the control server 102, the database cluster 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

In some embodiments, control server 102 is a computing system or platform made up of one or more computing devices. Embodiments of control server 102 may be a distributed computing system, a centralized computing system, a single computer such as a desktop or laptop computer or a networked computing system. Thus, in some embodiments, control server 102 comprises a multi-agent computer system with software agents.

Figure 2:
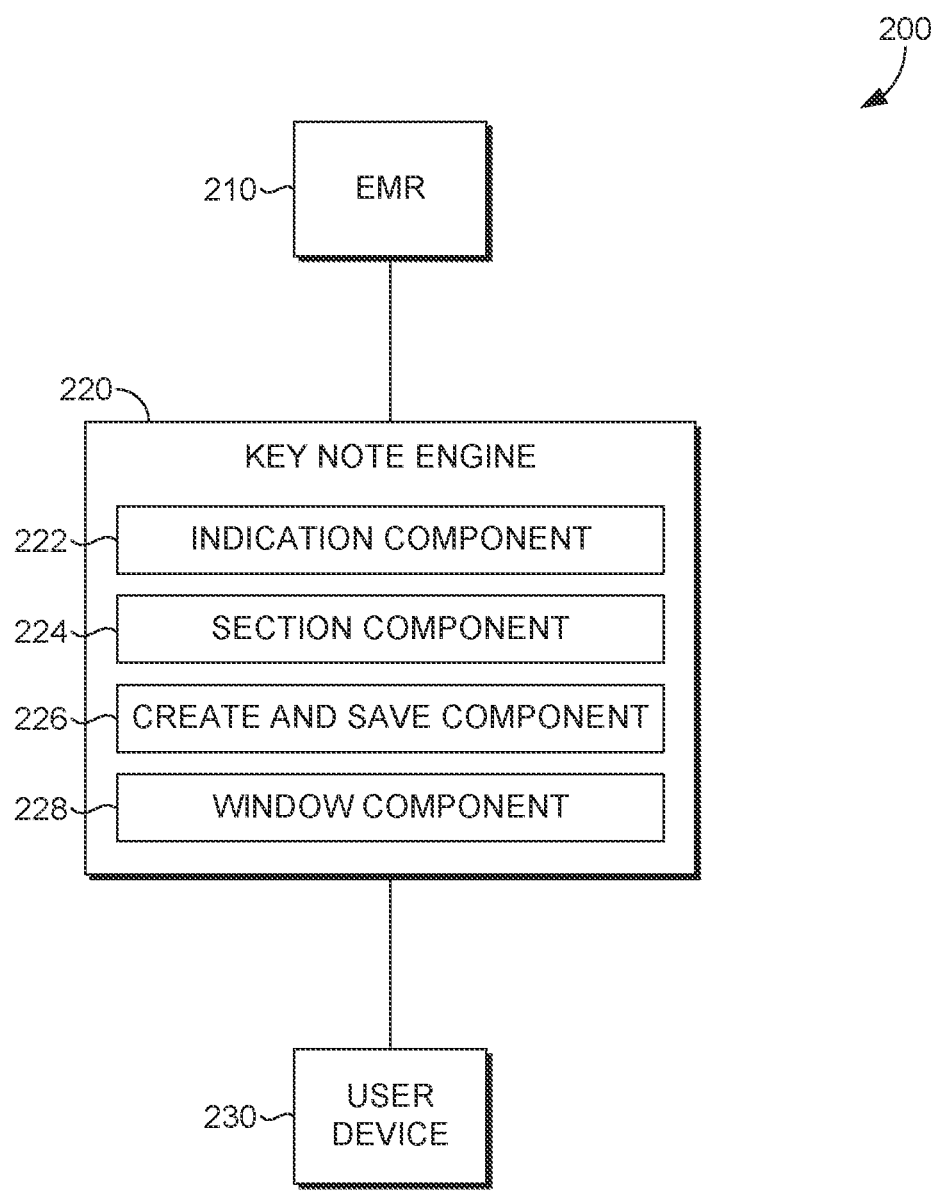
FIG. 2 is a block diagram of an exemplary system for creating and interacting with key notes, in accordance with an embodiment of the present invention.

Turning now to FIG. 2, an exemplary key note system 200 is depicted suitable for use in implementing embodiments of the present invention. The key note system 200 is merely an example of one suitable computing system environment and is not intended to suggest any limitation as to the scope of use or functionality of embodiments of the present invention. Neither should the key note system 200 be interpreted as having any dependency or requirement related to any single module/component or combination of modules/components illustrated therein.

The key note system 200 includes EMR 210, key note engine 220, and user device 230, all in communication with one another via a network. The network may include, without limitation, one or more secure local area networks (LANs) or wide area networks (WANs). The network may be a secure network associated with a facility such as a healthcare facility. The secure network may require that a user log in and be authenticated in order to send and/or receive information over the network.

The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, key note engine 220 or components of key note engine 220 might reside on a server, cluster of servers, or a computing device remote from one or more of the remaining components. Although illustrated as a single system, components of key note engine 220, the functionality provided by each of these components might be provided as separate components/modules. The single unit depiction is meant for clarity, not to limit the scope of embodiments in any form. In some embodiments, some or all functionality provided by the key note engine 220 (or any of its components) may be provided by a user device. Additionally, other components not shown may also be included within the network environment.

Components of the key note system 200 may include a processing unit, internal system memory, and a suitable system bus for coupling various system components, including one or more data stores for storing information (e.g., files and metadata associated therewith). Components of the key note system 200 typically includes, or has access to, a variety of computer-readable media.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

User device 230 includes or has access to infrastructure that is capable of receiving and storing information for use by, for example, key note engine 220 and/or EMR 210. The information received and stored in association with user device 230 may comprise key notes created by key note engine 220 and/or original information (e.g. summary notes) stored at EMR 210. User device 230 may receive data from other systems (e.g., disparate healthcare systems), which may include any number or type of medical devices that may be utilized to provide or measure patient care to a patient.

User device 230 may be any type of computing device used within a healthcare facility or as part of the claims processing process to receive, display, and send information to another user or system. User device 230 may be capable of communicating via the network with EMR 210 and/or key note engine 220. Such devices may include any type of mobile and portable devices including cellular telephones, personal digital assistants, tablet PCs, smart phones, and the like.

User device 230 is configured to display information to a user via a display. The information may include communications initiated by and/or received by EMR 210 and/or key note engine 220. For example, user device 230 is configured to display user interfaces provided by key note engine 220 that may include details stored by EMR 210, as described in more detail below. Embodiments are not intended to be limited to visual display but rather may also include audio presentation, visual presentation, combined audio/visual presentation, and the like.

Key note engine 220 and/or user device 230 includes or has access to infrastructure that is capable of storing electronic medical records (EMRs), such as EMR 210, of patients associated with user device 230. EMRs may comprise electronic clinical documents such as images, clinical notes, orders, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, alert history, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information.

In some embodiments, key note engine 220 and/or user device 230 may receive or utilize data from health information exchanges ("HIEs"), personal health records ("PHRs"), patient claims, and other health records associated with a patient. For example, key note engine 220 may utilize data from these sources to create key notes and user device 230 may access original information stored by these sources when interacting with key notes. Although described with respect to healthcare information, it is contemplated key note engine 220 and/or user device 230 may receive any type of records or information received from other systems, which may include any number or type of devices that may be utilized to provide or measure any data that may benefit a user when creating or interacting with key notes.

Generally, key note engine 220 is configured to enable users (e.g., clinicians) to create and interact with snapshots (i.e., key notes) of critical clinical/non-clinical information that is readily accessible in future visits. When a document or note is created, the text or information from the note can be selected and marked as a key note. To do so, in one embodiment, a user selects the text or information and right clicks to select "Key Note." Upon doing so, sections are displayed, such as "General Notes," Diagnosis," "Medication," "Results," and "Others." These sections enable a user to categorize the data in a key note so it can be saved and displayed under the selected section. Key note engine 210 includes several components including indication component 222, section component 224, create and save component 226, and window component 228.

The indication component 222 generally enables the user to select the text or information from a document or note. While the user is creating or reviewing the document or note, the indication component 222 enables the user to select the desired text or information, right click, and create the key note. In some embodiments, if the document or note is being created, rather than reviewed, the key note is only created upon the user signing or verifying the document or note.

The section component 224 generally enables the user to categorize the key note. While creating the key note, the user is presented with various predefined sections under which the key note will be saved, and later displayed, in the key note window. For example, the sections may include "General Notes," "Diagnosis," "Medications," "Results," and "Others." For clarity, "Others" represents a customized section that enables the user to define the name of the section. When the user selects "Others," another window opens that enables the user to specify a customized name of the section. The section component 224 displays the customized section when the user selects text or information during or while interacting with documentation from the same visit or encounter. The customized section is also displayed as a key note by the section component 224, along with other sections, under the customized name of the section in the key note window. For example, if the user selects "General Notes," "Diagnosis," "Medications," or "Results," the section component 224 displays the key note under the respective section in the key note window.

The create and save component 226 generally creates the key note. As mentioned above, a key note is only created upon the user signing or verifying the document or note. If the user fails to sign or verify the document or note, a key note is not created and will not be displayed by key note window.

The window component 228 generally provides a place holder to display all key notes that have been created for visits or encounters of a patient. In embodiments, the window component 228 launches the key note window upon a user selecting a key note window icon. In some embodiments, the key note window displays the key notes with recent the most visit/encounter at the top followed by older visits/encounters in descending order. The key notes may be collapsed by default to save room in the key note window and only display summary information in a header. For example, the header may display the visit/encounter date followed by a diagnosis and a type of the visit. The diagnosis displayed may represent the discharge diagnosis type whose status can be anything but not cancelled.

In some embodiments, the window component 228 enables the user to remove or delete the key note for the visit/encounter from the key note window (such as by selecting a remove or delete icon, which may be symbolized by an "X"). A warning message may be displayed to make sure the user wants to delete the key note permanently. Upon confirming the intention to delete the key note permanently, the key note is deleted permanently and is no longer is displayed in the key note window (for the current visit or any upcoming visits).

In some embodiments, the user may select a particular key note to expand the key note and provide additional details. In the expanded key note, the section name may be displayed followed by corresponding section data that has been saved. Only sections under which the text or information was saved is displayed. On one side of the expanded section, the original summary notes from which the key note was created may be displayed as a hyperlink. Upon selecting the hyperlink, the user can access the original summary notes to view additional details.

With reference to FIGS. 3-14, illustrative screen displays 300, 400, 500 . . . 1400 of embodiments of the present invention are shown. It is understood that each of the illustrative screen displays are connected logically, such that they comprise a user interface designed for creating and interacting with key notes. The screen displays may appear in any order and with any number of screen displays, without regard to whether the screen display is described or depicted herein. The screen displays provide tools that enable creating and interacting with key notes in accordance with embodiments of the present invention. For clarity, although the terms Power Note, dynamic documentation, and clinical note are used herein, they are not specific to any particular solution and may encompass any notes or documents which are utilized to capture the information of and during a patient visit.

Figure 3:
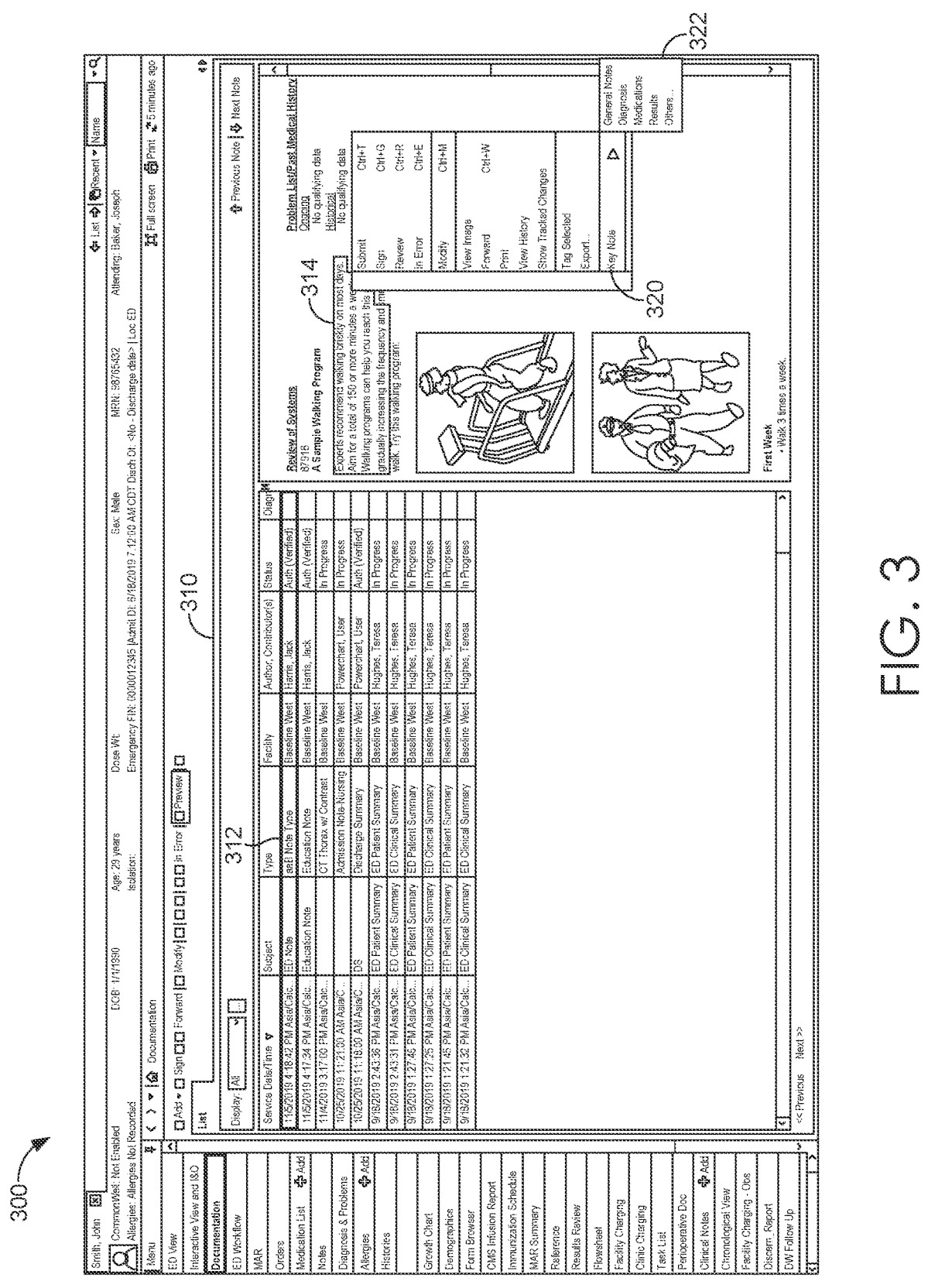

Referring initially to FIG. 3, user interface 300 depicts creating a key note from signed, verified dynamic documentation. As illustrated, a user may be reviewing dynamic documentation 310 corresponding to a patient. The user may select the dynamic documentation corresponding to a particular encounter 312. The user may select text or information 314 for that encounter 312 to generate a key note. For example, the user may highlight the selected text or information 314 and right click and select "Key Note" 320. Upon selecting "Key Note" 320, user interface 300 provide sections 322 that enable the user to save and display the selected text/data under a selected section for key note.

For example, if the selected text/data is associated with general notes, the user can save the selected text/data under "General Notes." If the selected text/data is associated with a diagnosis, the user can save selected text/data under "Diagnosis." If selected text/data is associated with a medication, the user can save selected text/data under "Medication." If selected text/data is associated with results, the user can save the selected text/data under "Results." If the selected text/data is not associated with general notes, diagnosis, medication, or results, the user can save selected text/data under "Others," which allows the user to create a custom section for selected text/data in a key note.

Figure 4:
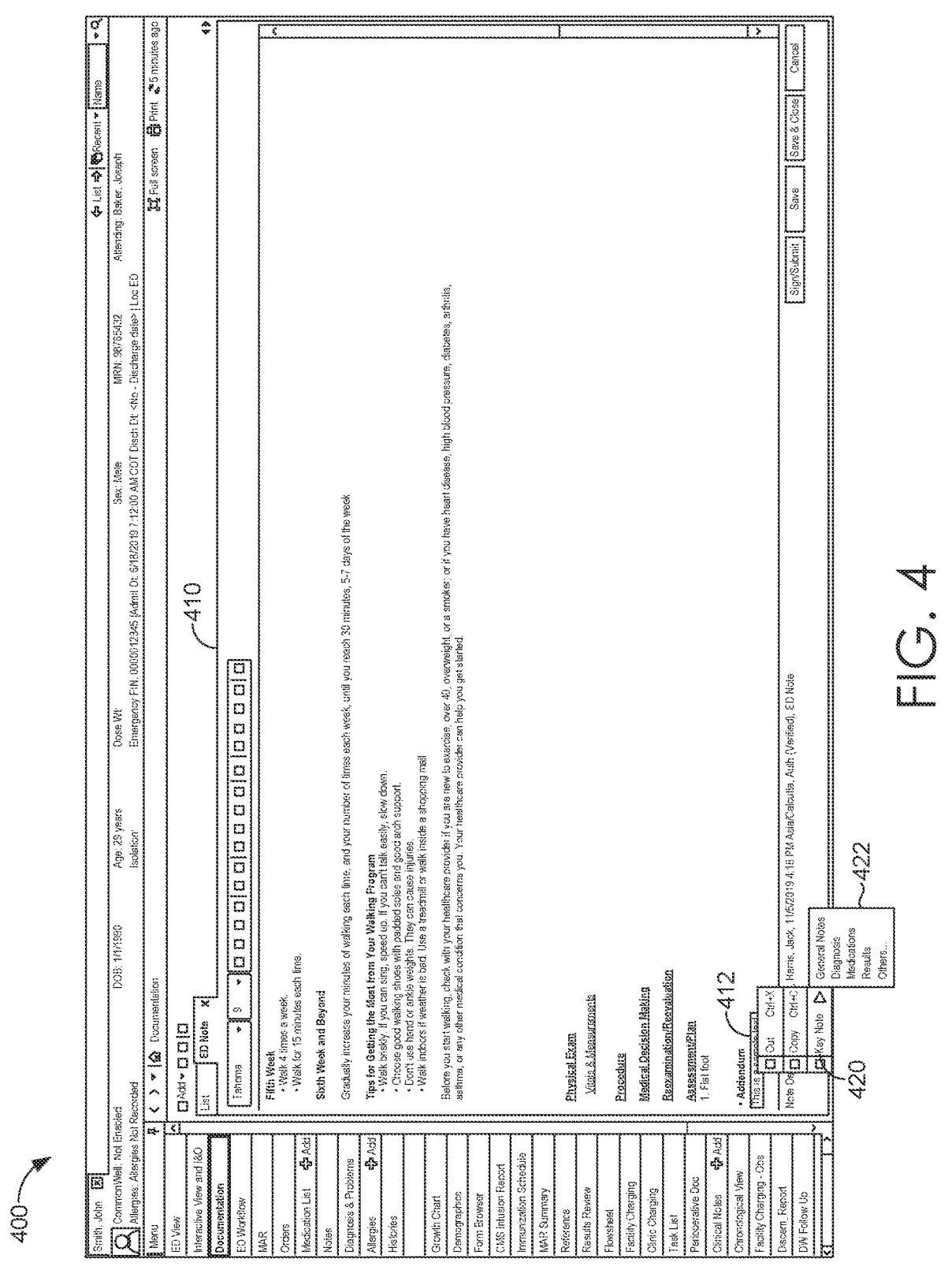

In FIG. 4, user interface 400 illustrates creating a key note when signed, verified dynamic documentation is being modified. In the example, the dynamic documentation is an emergency department (ED) note 410. As shown, the user may select text or information 412 for that ED note 410 to generate a key note. Upon right clicking the selected text or information 412 and selecting "Key Note" 420, user interface 400 provides sections 422, such as the sections described with respect to FIG. 3.

Figure 5:
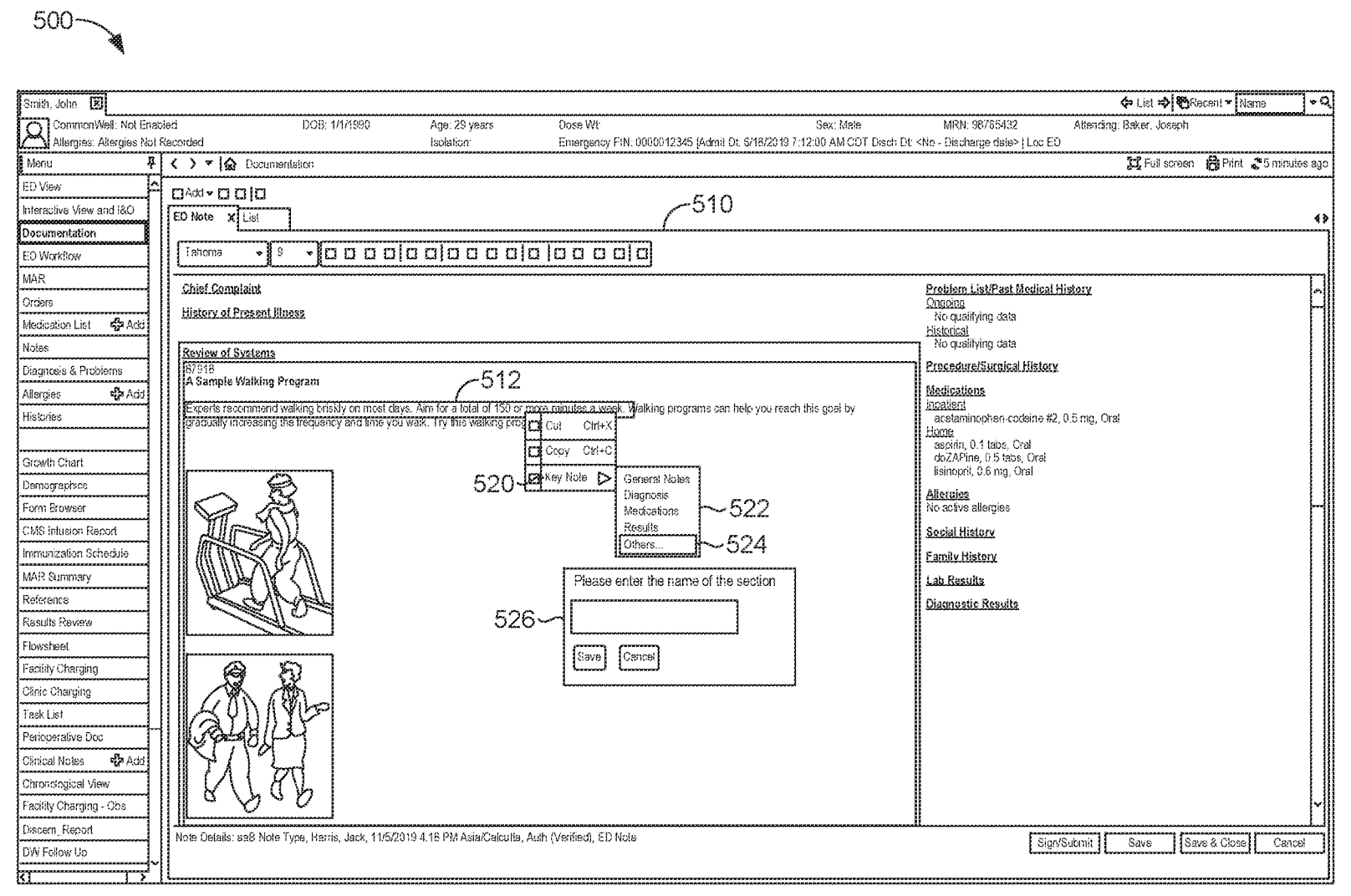

Turning now to FIG. 5, user interface 500 depicts creating a key note from dynamic documentation by selecting "Others" as the section. As shown, the user may select text or information 512 from the dynamic documentation. Upon right clicking the selected text or information 512 and selecting "Key Note" 520, user interface 500 provides sections 522, such as the sections described with respect to FIG. 3. However, in this example, the user selects "Others" 524 and a prompt 526 is presented to the user to enter the name of the section.

Figure 6:
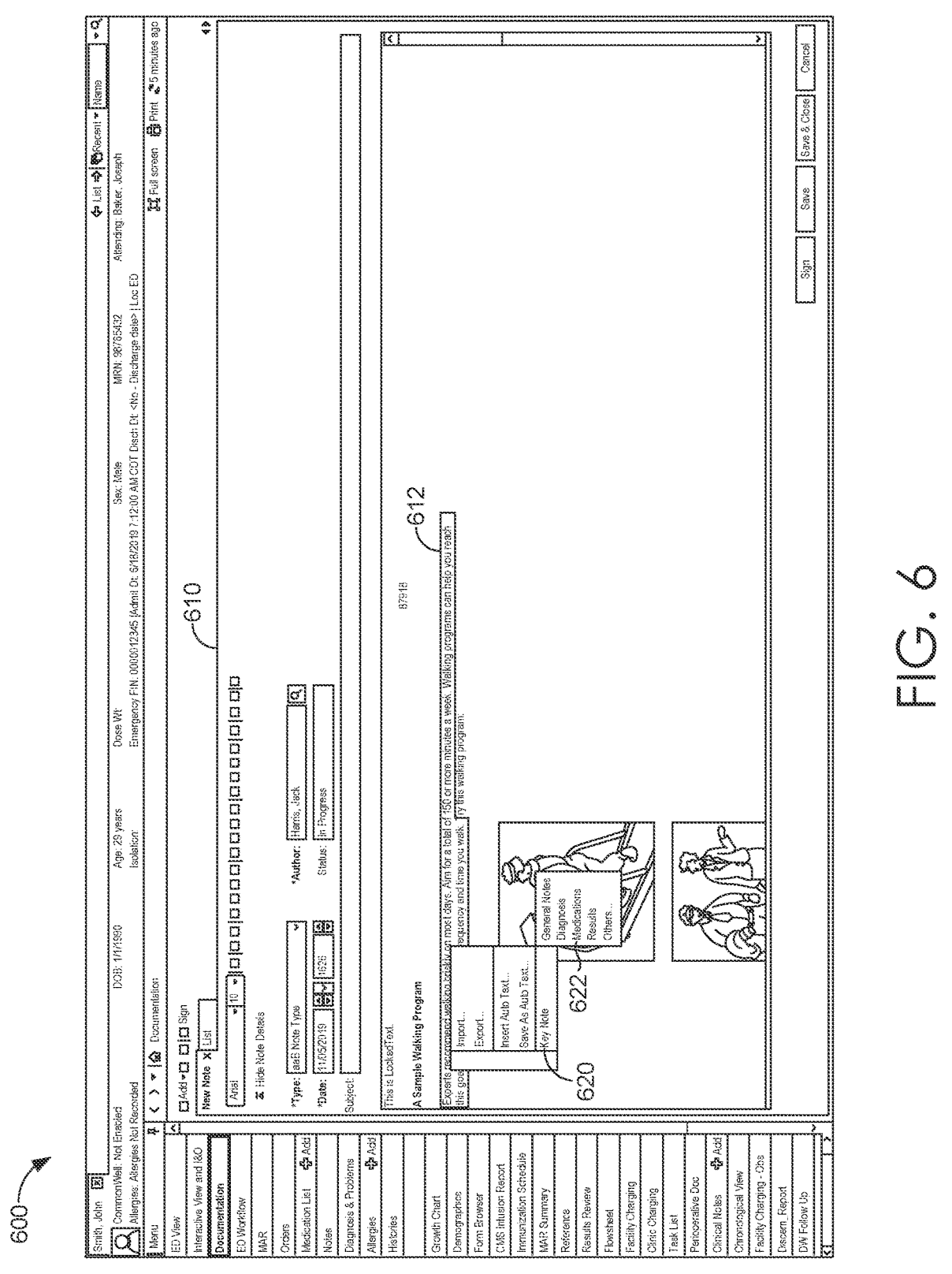

Referring to FIG. 6, user interface 600 illustrates creating a key note when a clinical note is being created and saved/signed. As illustrated, a user may be creating a clinical note 610 corresponding to a patient. The user may select text or information 612 corresponding to a portion of the clinical note 610 to generate a key note. For example, the user may highlight the selected text or information 612 and right click and select "Key Note" 620. Upon selecting "Key Note" 620, user interface 600 provide sections 622 that enable the user to save and display the selected text/data under a selected section, such as the sections described with respect to FIG. 3.

Figure 7:
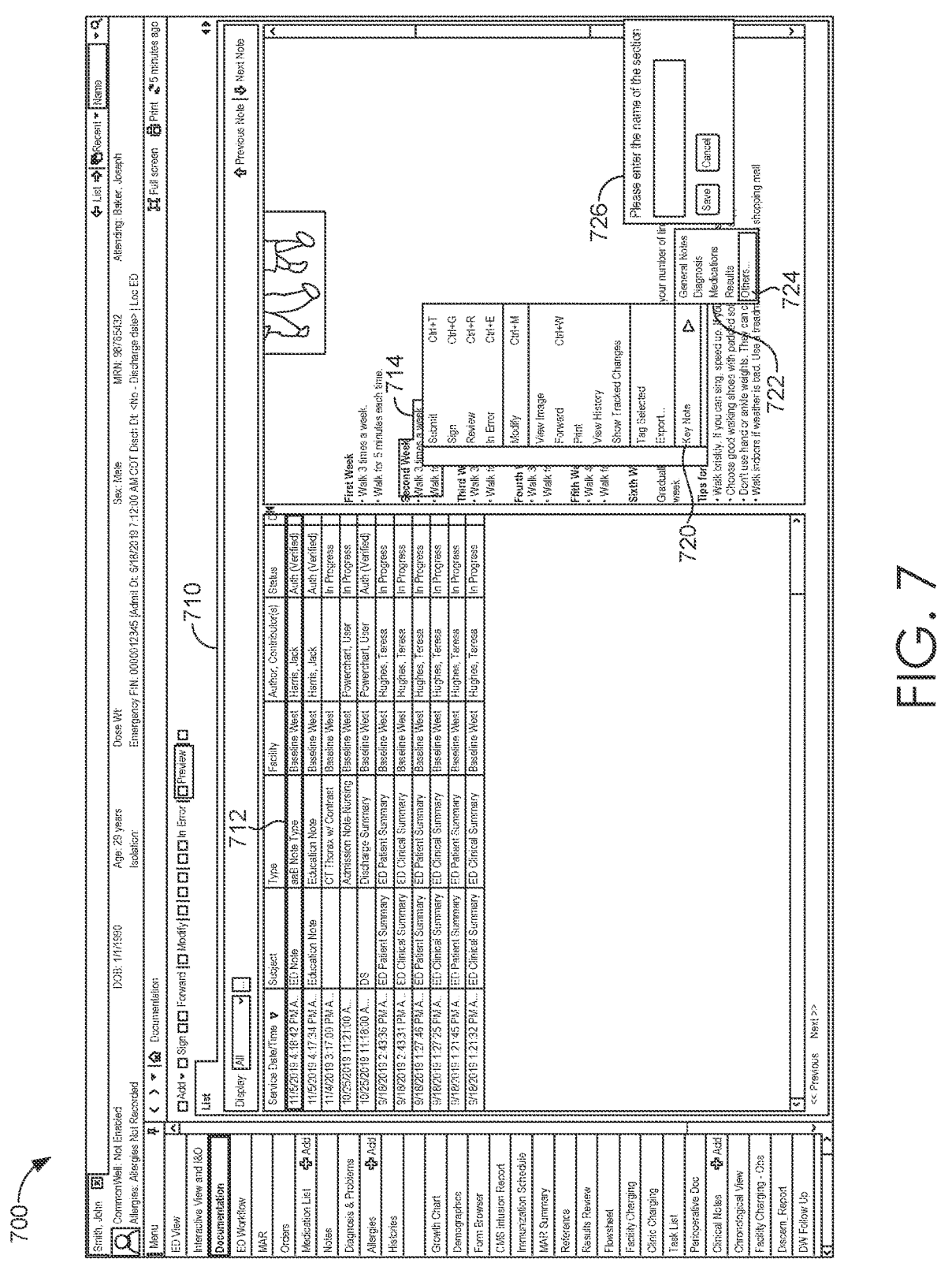

In FIG. 7, user interface 700 depicts creating a key note after a clinical note is signed and verified. As illustrated, the user may select a particular clinical note 712. The user may select text or information 714 for that clinical note to generate a key note. For example, the user may highlight the selected text or information 714 and right click and select "Key Note" 720. Upon selecting "Key Note" 720, user interface 700 provide sections 722 that enable the user to save and display the selected text/data under a selected section In this example, the user selects "Others" 724 and a prompt 726 is presented to the user to enter the name of the section.

Figure 8:
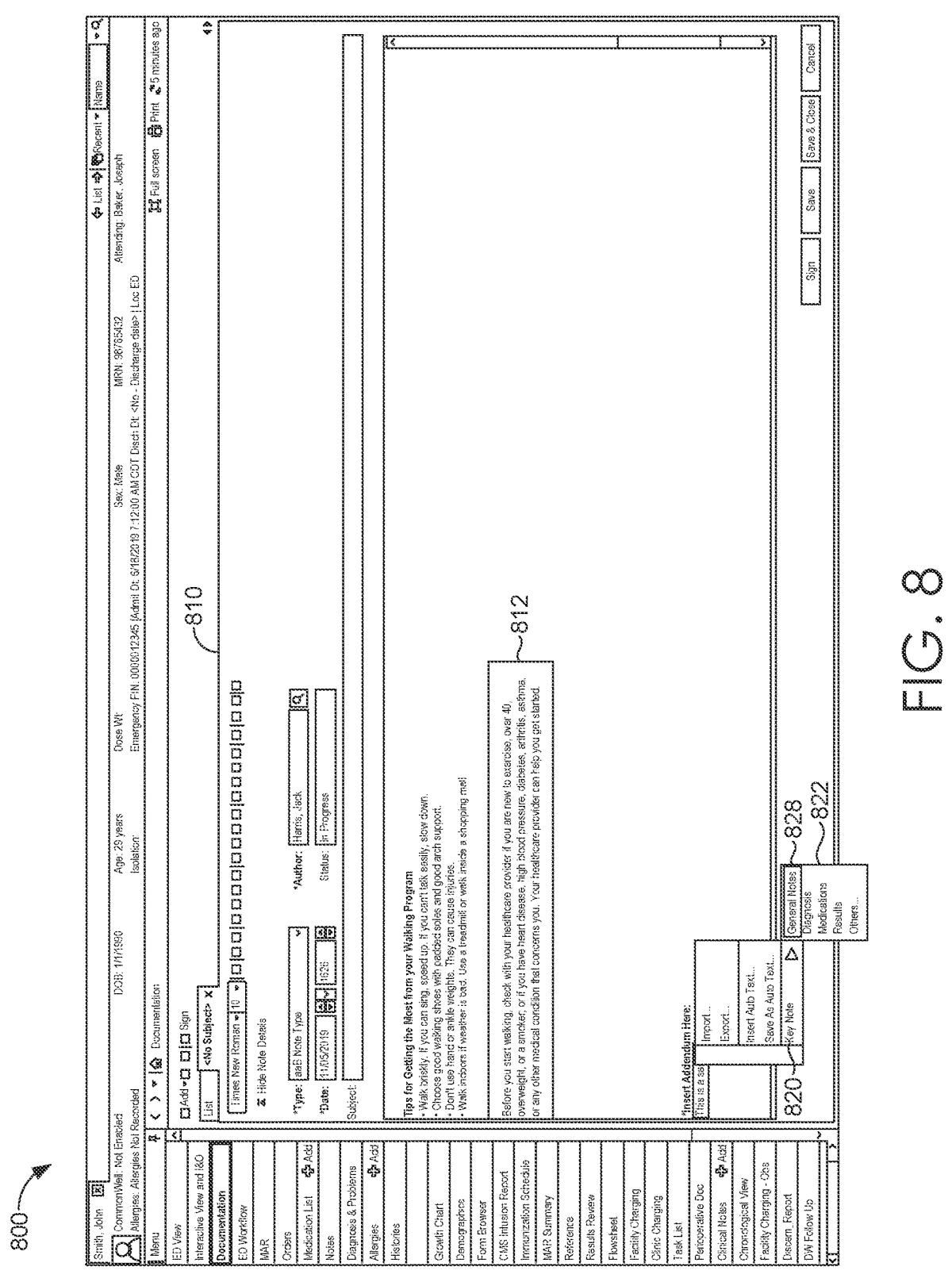

Turning now to FIG. 8, user interface 800 illustrates creating a keynote when a signed, verified clinical note is being modified. As shown, the user may select text or information 812 for the clinical note 810 to generate a key note. Upon right clicking the selected text or information 812 and selecting "Key Note" 820, user interface 800 provides sections 822, such as the sections described with respect to FIG. 3. In this example, the user selects "General Notes" 928.

Figure 9:
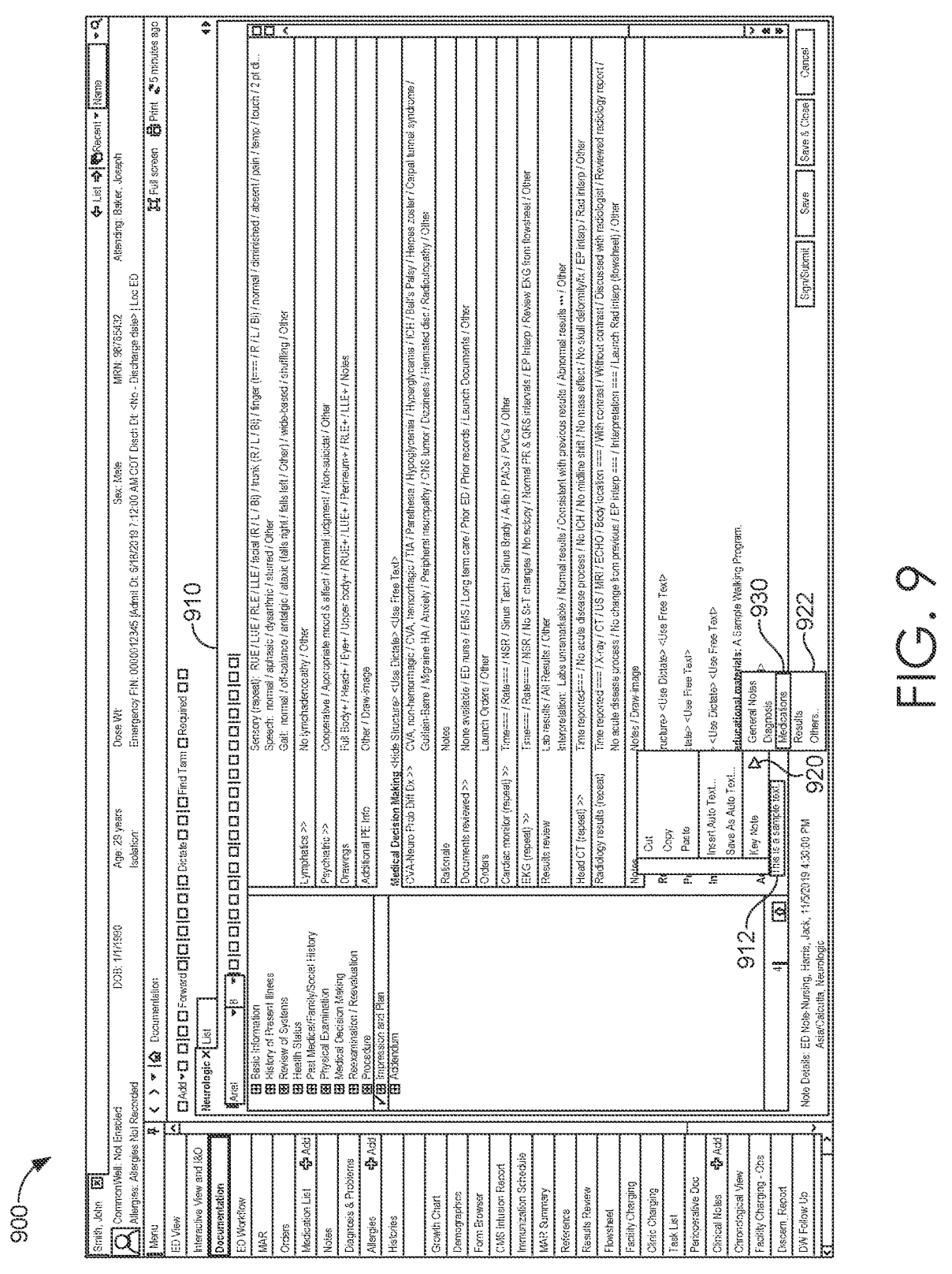

Referring to FIG. 9, user interface 900 illustrates creating a key note under the "Medication" section when a Power Note is being created and saved. As illustrated, a user may be creating a Power Note 910 corresponding to a patient. The user may select text or information 912 corresponding to a portion of the Power Note 910 to generate a key note. For example, the user may highlight the selected text or information 912 and right click and select "Key Note" 920. Upon selecting "Key Note" 920, user interface 900 provide sections 922 that enable the user to save and display the selected text/data under a selected section, such as the sections described with respect to FIG. 3. In this example, the user selects "Medications" 930.

Figure 10:
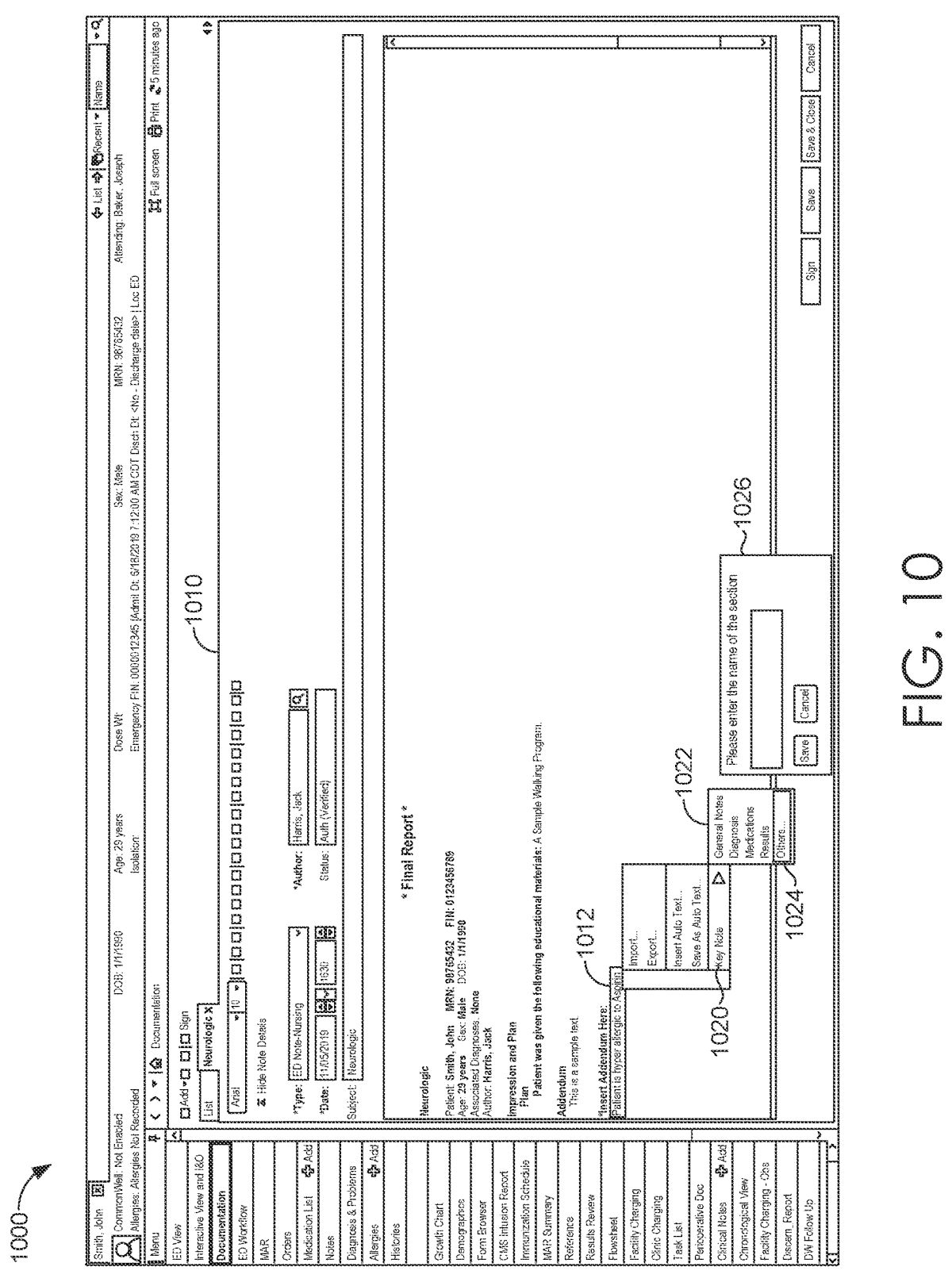

In FIG. 10, user interface 1000 illustrates creating a key note when a signed, verified Power Note is being modified. As shown, the user may select text or information 1012 for the Power Note 1010 to generate a key note. Upon right clicking the selected text or information 1012 and selecting "Key Note" 1020, user interface 1000 provides sections 1022, such as the sections described with respect to FIG. 3. In this example, the user selects "Others" 1024 and a prompt 1026 is presented to the user to enter the name of the section.

Figure 11:
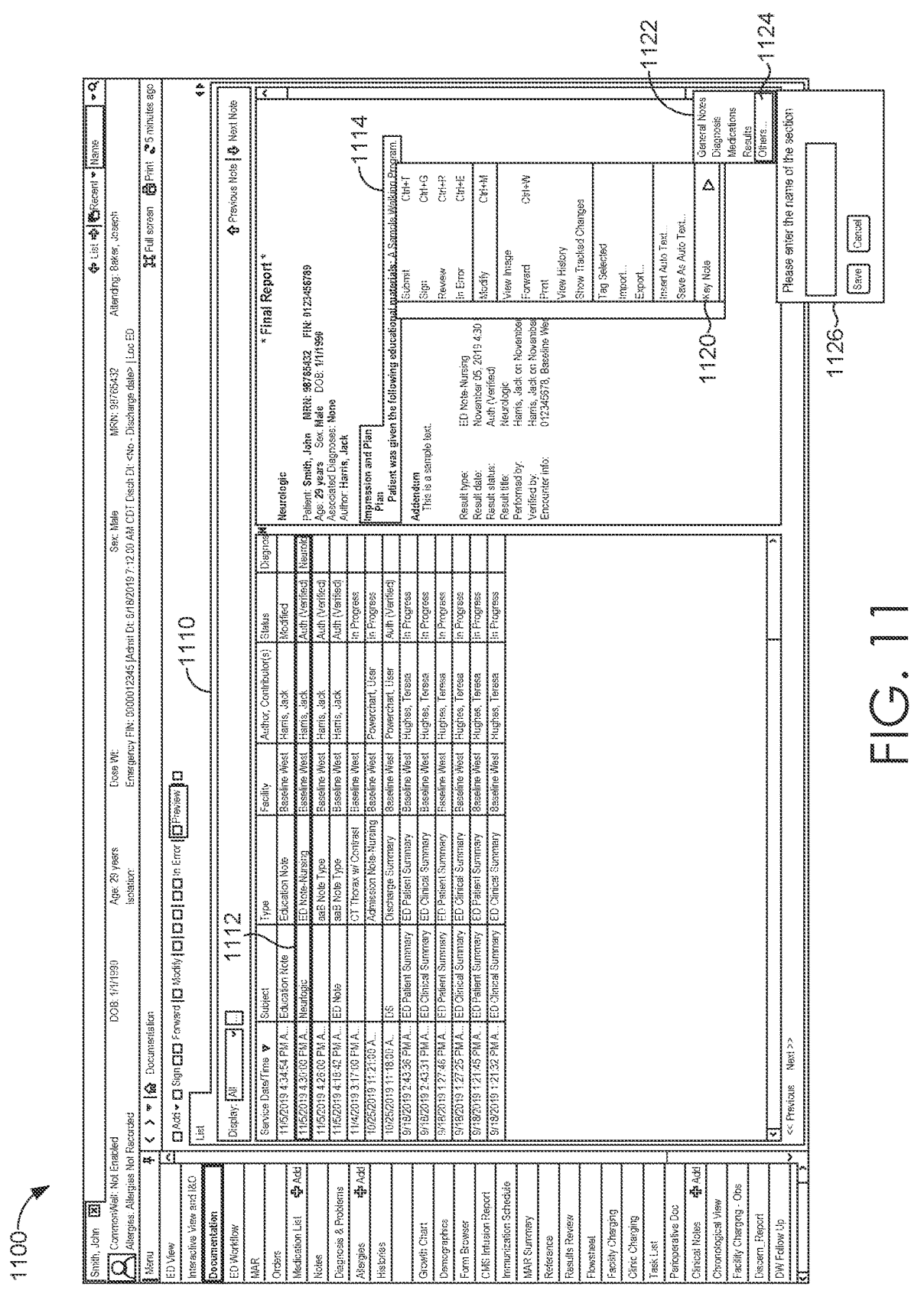

Turning now to FIG. 11, user interface 1100 depicts creating a key note after a Power Note is signed and verified. As illustrated, the user may select a particular Power Note 1112. The user may select text or information 1114 for that Power Note to generate a key note. For example, the user may highlight the selected text or information 1114 and right click and select "Key Note" 1120. Upon selecting "Key Note" 1120, user interface 1100 provide sections 1122 that enable the user to save and display the selected text/data under a selected section In this example, the user selects "Others" 1124 and a prompt 1126 is presented to the user to enter the name of the section.

Figure 12:
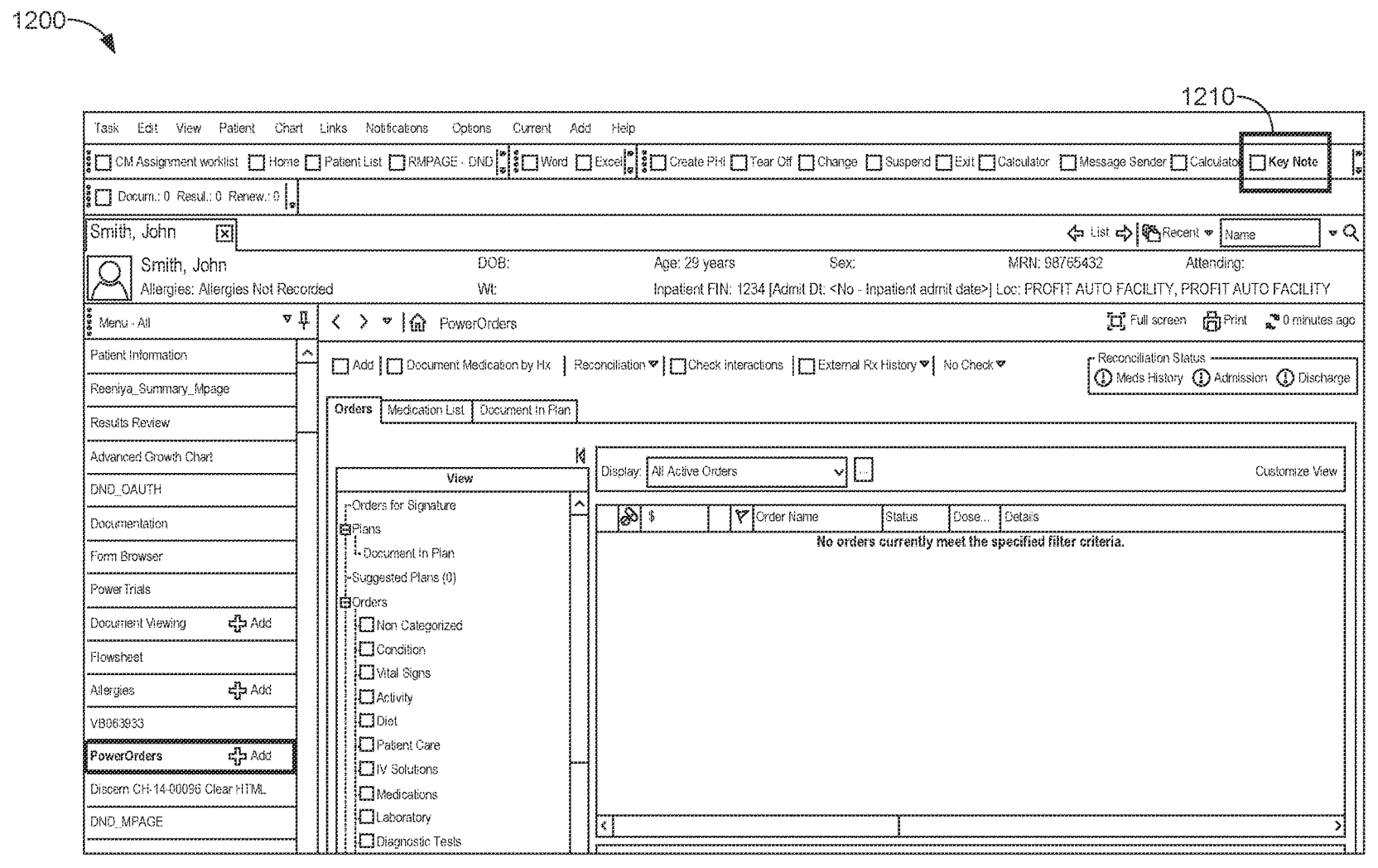
Figure 13:
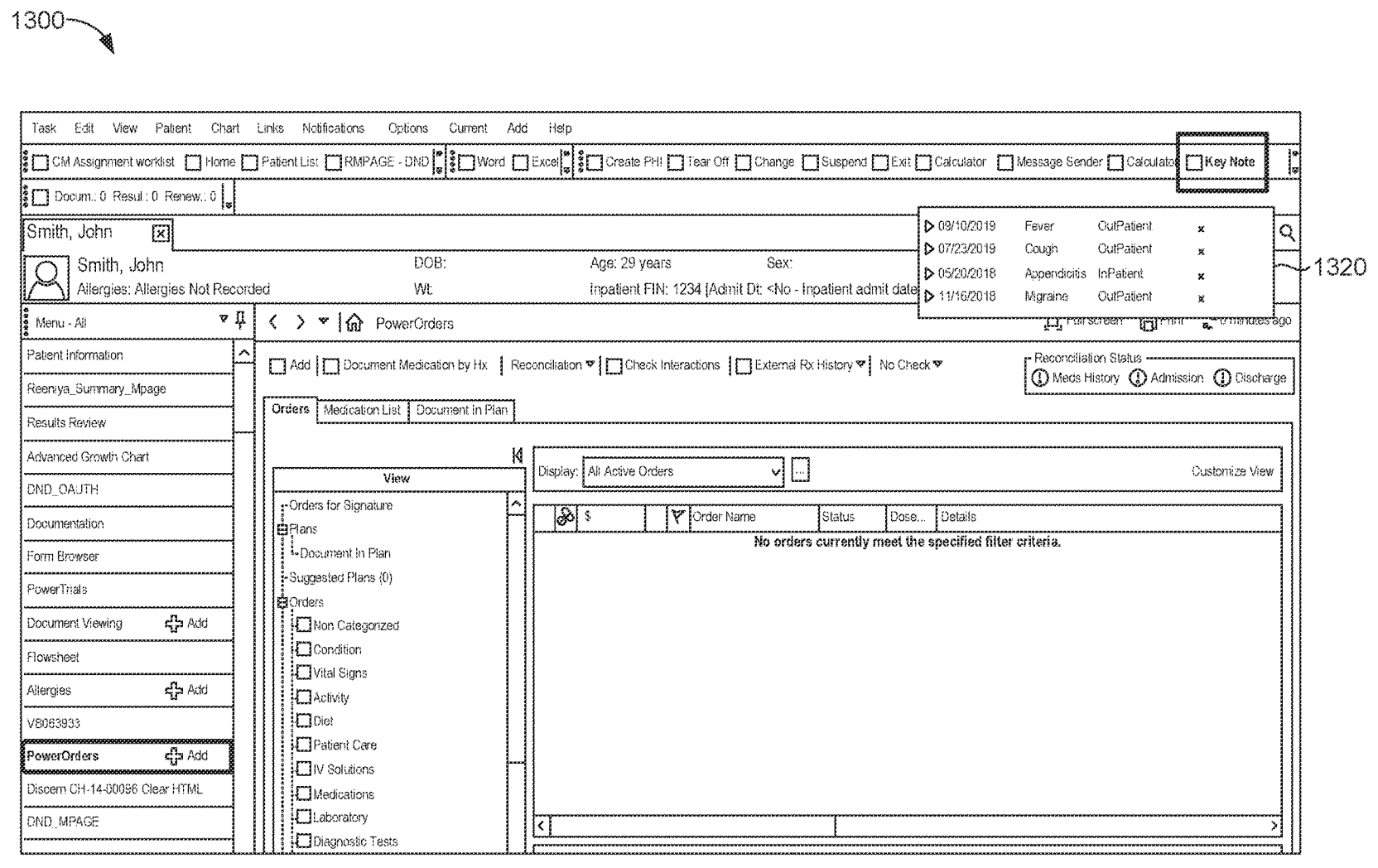
Figure 14:
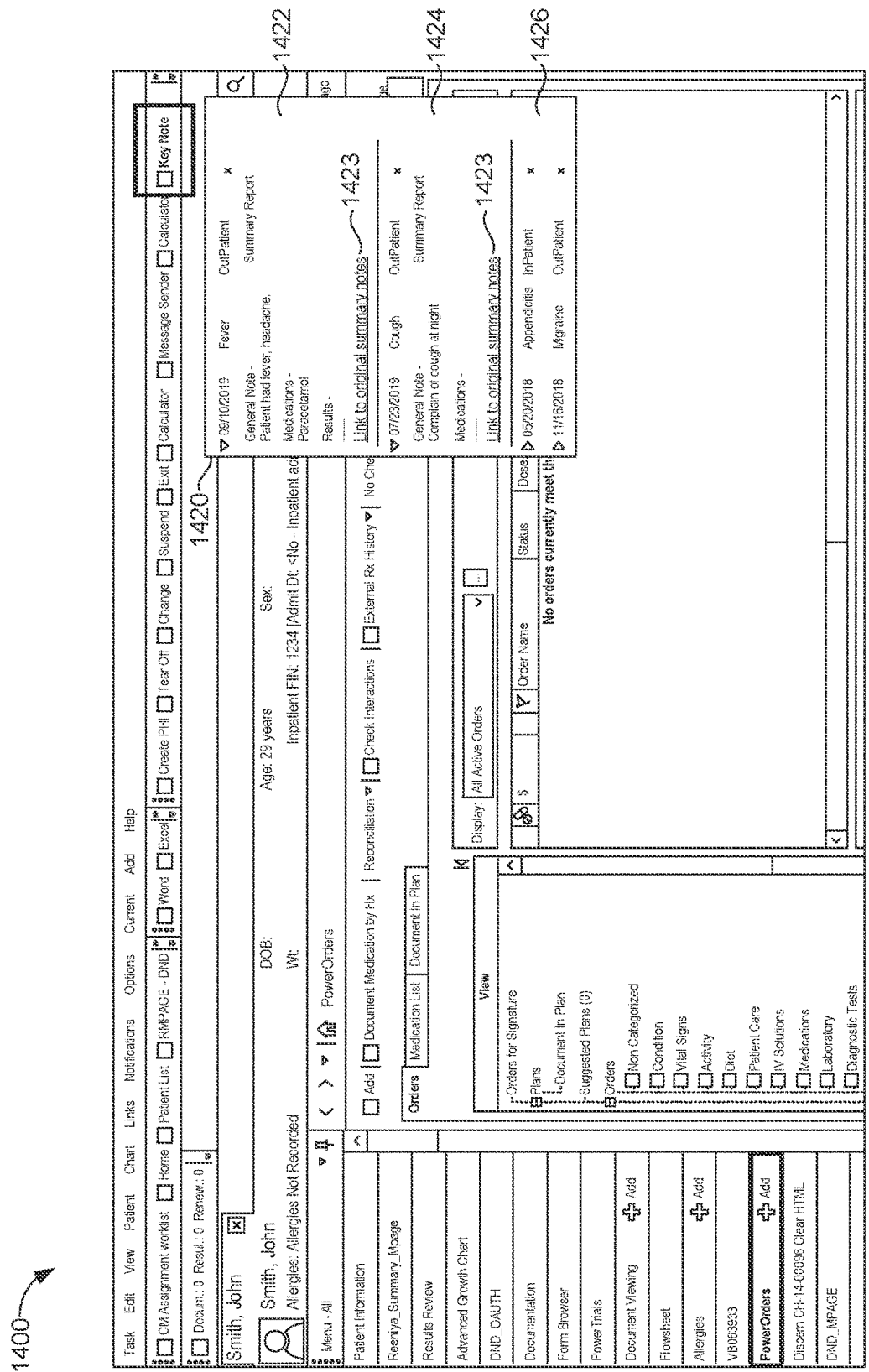

Referring to FIGS. 12-14, user interfaces 1200, 1300, 1400 illustrate interacting with key notes after they have been created. Initially, user interface 1200 illustrates launching the key note window by clicking the "Key Note" icon 1210 from the organization bar for a selected patient. All key notes 1320 are displayed in descending order based on the visit or encounter date, as shown in user interface 1300. The key notes are collapsed by default. In FIG. 14, user interface 1400 depicts displaying key note details for key notes 1420 that have been selected by the user and expanded. As shown, visits or encounters 1422, 1424 have been selected by the user and expanded and include key note details. In contrast, visits or encounters 1426 have not been selected by the user and remain collapsed and do not include key note details. Hyperlinks 1423, 1425 to original summary notes from which the particular key note was created may also be provided.

Figure 15:
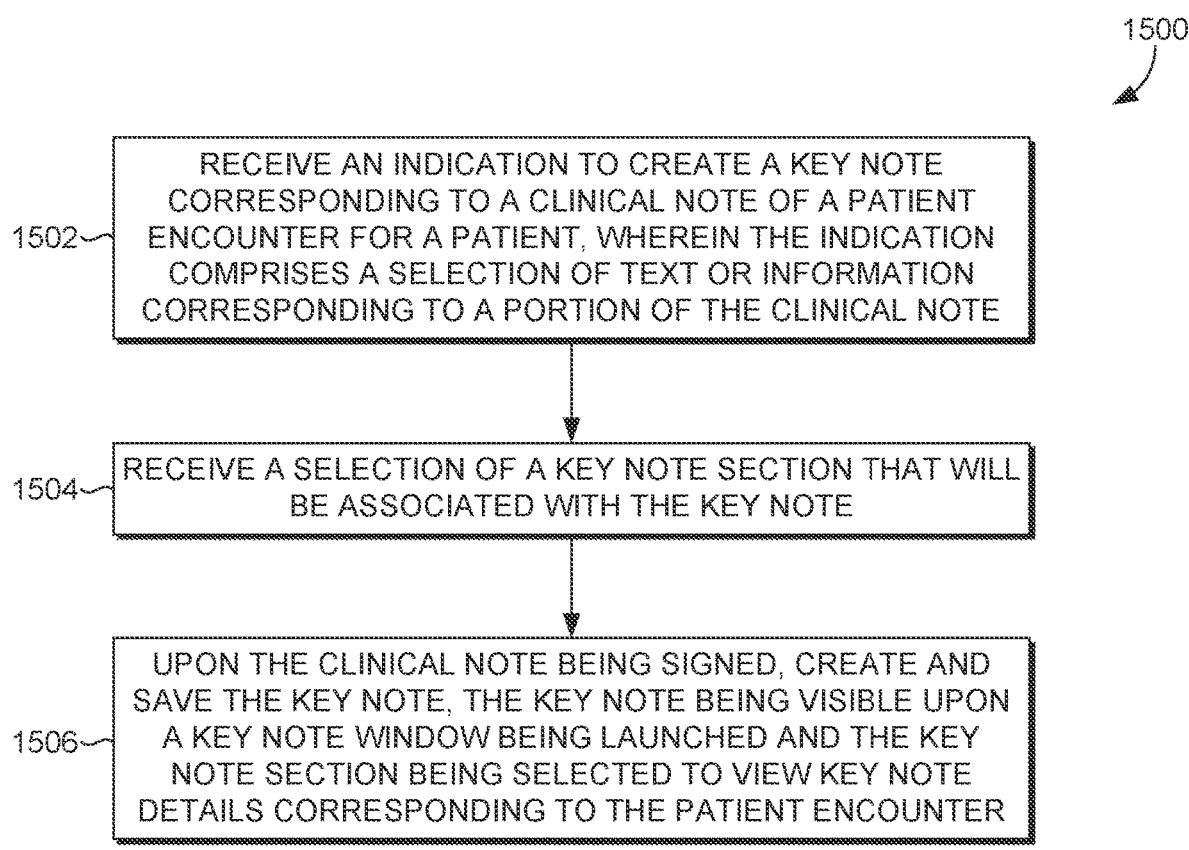
FIG. 15 is a flow diagram showing an exemplary method for creating key notes, in accordance with various embodiments of the present invention.

Turning now to FIG. 15, a flow diagram is provided illustrating a method 1500 for creating key notes, in accordance with an embodiment of the present invention. Method 1500 may be performed by any computing device (such as computing device described with respect to FIG. 1) with access to a key note system (such as the one described with respect to FIG. 2) or by one or more components of the key note system.

Initially, as shown at step 1502, an indication to create a key note corresponding to a clinical note of a patient encounter for a patient is received. The indication comprises a selection of text or information corresponding to a portion of the clinical note.

At step 1504, a selection of a key note section that will be associated with the key note is received.

At step 1506, upon the clinical note being signed, the key note is created and saved. The key note is visible upon a key note window being launched and the key note section being selected to view key note details corresponding to the patient encounter.

Figure 16:
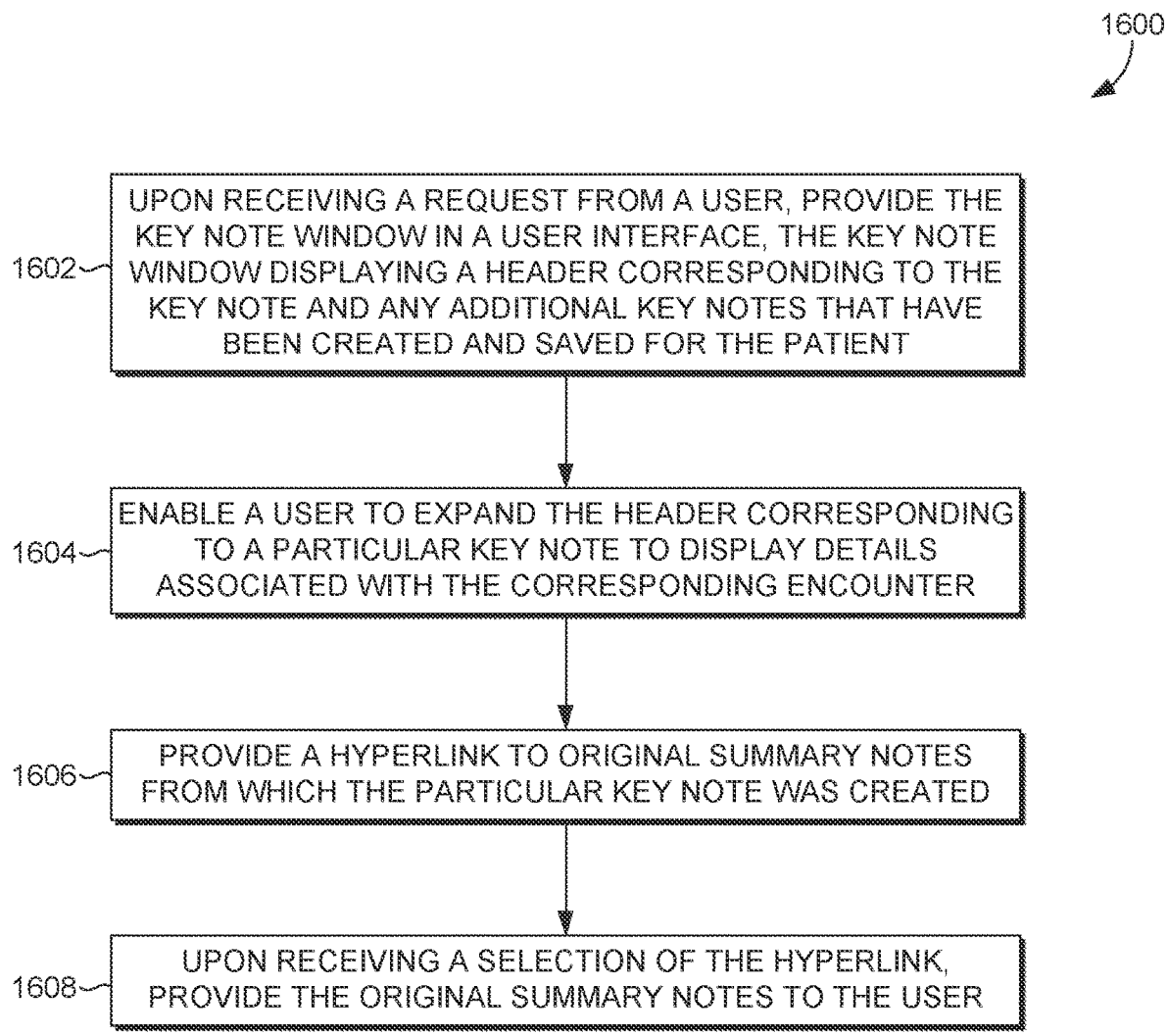
FIG. 16 is a flow diagram showing an exemplary method for interacting with key notes, in accordance with various embodiments of the present invention.

Referring now to FIG. 16, a flow diagram is provided illustrating a method 1600 for interacting with key notes, in accordance with an embodiment of the present invention. Method 1600 may be performed by any computing device (such as computing device described with respect to FIG. 1) with access to a key note system (such as the one described with respect to FIG. 2) or by one or more components of the key note system.

Initially, as shown at step 1602, upon receiving a request from a user, the key note window is provided in a user interface. The key note window displays a header corresponding to the key note and any additional key notes that have been created and saved for the patient. The header may comprise an encounter date, a diagnosis, and a type of encounter. In some embodiments, the key note and the additional key notes are presented in the key note window in chronological order corresponding to an encounter date of each key note.

At step 1604, a user is enabled to expand the header corresponding to a particular key note to display details associated with the corresponding encounter.

At step 1606, a hyperlink to original summary notes from which the particular key note was created is provided.

At step 1608, upon receiving a selection of the hyperlink, the original summary notes are provided to the user.

As can be understood, the present invention provides systems, methods, and user interfaces for creating and interacting with key notes. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more computer storage media having computer-executable instructions embodied thereon, that when executed, perform operations, the operations comprising:
    receiving an indication to create a key note corresponding to a clinical note of a patient encounter for a patient, wherein the indication comprises a selection of text or information corresponding to a portion of the clinical note;
    receiving a selection of a key note section that will be associated with the key note;
    upon the clinical note being signed, creating and saving the key note, the key note being visible upon a key note window being launched and the key note section being selected to view key note details corresponding to the patient encounter; and
    enabling the key note to be deleted.

2. The media of claim 1, further comprising, upon receiving a request from a user, providing the key note window in a user interface, the key note window displaying a header corresponding to the key note and any additional key notes that have been created and saved for the patient.

3. The media of claim 2, wherein the key note and the additional key notes are presented in the key note window in chronological order corresponding to an encounter date of each key note.

4. The media of claim 3, wherein the header comprises an encounter date, a diagnosis, and a type of encounter.

5. The media of claim 2, further comprising, enabling a user to expand the header corresponding to a particular key note to display details associated with the corresponding encounter.

6. The media of claim 5, further comprising providing a hyperlink to original summary notes from which the particular key note was created.

7. The media of claim 6, further comprising, upon receiving a selection of the hyperlink, providing the original summary notes to the user.

8. A computerized method comprising:
    receiving an indication to create a key note corresponding to a clinical note of a patient encounter for a patient, wherein the indication comprises a selection of text or information corresponding to a portion of the clinical note;
    receiving a selection of a key note section that will be associated with the key note;
    upon the clinical note being signed, creating and saving the key note, the key note being visible upon a key note window being launched and the key note section being selected to view key note details corresponding to the patient encounter; and
    enabling the key note to be deleted.

9. The method of claim 8, further comprising, upon receiving a request from a user, providing the key note window in a user interface, the key note window displaying a header corresponding to the key note and any additional key notes that have been created and saved for the patient.

10. The method of claim 9, wherein the key note and the additional key notes are presented in the key note window in chronological order corresponding to an encounter date of each key note.

11. The method of claim 10, wherein the header comprises an encounter date, a diagnosis, and a type of encounter.

12. The method of claim 9, further comprising, enabling a user to expand the header corresponding to a particular key note to display details associated with the corresponding encounter.

13. The method of claim 12, further comprising providing a hyperlink to original summary notes from which the particular key note was created.

14. The method of claim 13, further comprising, upon receiving a selection of the hyperlink, providing the original summary notes to the user.

15. A computerized system comprising:

one or more processors; and a non-transitory computer storage media storing computer-useable instructions that, when used by the one or more processors, cause the one or more processors to:

receive an indication to create a key note corresponding to a clinical note of a patient encounter for a patient, wherein the indication comprises a selection of text or information corresponding to a portion of the clinical note;

receive a selection of a key note section that will be associated with the key note;

upon the clinical note being signed, create and save the key note, the key note being visible upon a key note window being launched and the key note section being selected to view key note details corresponding to the patient encounter;

upon receiving a request from a user, provide the key note window in a user interface, the key note window displaying a header corresponding to the key note and any additional key notes that have been created and saved for the patient; and enable the key note to be deleted.

16. The system of claim 15, wherein the key note and the additional key notes are presented in the key note window in chronological order corresponding to an encounter date of each key note.

17. The system of claim 16, wherein the header comprises an encounter date, a diagnosis, and a type of encounter.

18. The system of claim 15, further comprising, enabling a user to expand the header corresponding to a particular key note to display details associated with the corresponding encounter.

19. The system of claim 18, further comprising providing a hyperlink to original summary notes from which the particular key note was created.

20. The system of claim 19, further comprising, upon receiving a selection of the hyperlink, providing the original summary notes to the user.

* * * * *